(12) United States Patent
Almog

(10) Patent No.: US 6,859,522 B2
(45) Date of Patent: Feb. 22, 2005

(54) CAROTID ARTERY FILTER SYSTEM FOR SINGLE VIEW DENTAL PANORAMIC RADIOGRAPHS

(75) Inventor: Dov M. Almog, Pittsford, NY (US)

(73) Assignee: University of Rochester Medical Center, Rochester, NY (US)

( * ) Notice: Subject to any disclaimer, the term of this patent is extended or adjusted under 35 U.S.C. 154(b) by 0 days.

(21) Appl. No.: 10/244,103

(22) Filed: Sep. 13, 2002

(65) Prior Publication Data

US 2004/0052329 A1 Mar. 18, 2004

(51) Int. Cl.[7] .................................................. G21K 3/00
(52) U.S. Cl. ...................................... 378/156; 378/185
(58) Field of Search ................................ 378/156–159, 378/185–187

(56) References Cited

U.S. PATENT DOCUMENTS

| | | | |
|---|---|---|---|
| 3,569,712 A | 3/1971 | Avakoff | |
| 3,976,889 A | 8/1976 | Noske et al. | |
| 4,082,957 A | 4/1978 | Morlan | |
| 4,497,062 A * | 1/1985 | Mistretta et al. | 378/158 |
| 4,641,336 A | 2/1987 | Gastrin | |
| 4,788,699 A | 11/1988 | Dobert et al. | |
| 5,454,023 A | 9/1995 | Asikainen | |
| 5,734,693 A | 3/1998 | Quint et al. | |
| 6,220,751 B1 * | 4/2001 | DiGiacomo et al. | 378/182 |

* cited by examiner

Primary Examiner—Craig E. Church
(74) Attorney, Agent, or Firm—Townsend & Townsend & Crew LLP

(57) ABSTRACT

A method and a suite of filters for detecting carotid artery calcification in a panoramic dental radiograph, including imposing a filter between an x-ray radiation beam source and an imaging medium, wherein the imposing attenuates the effect of the incident x-ray in the region of the carotid artery; obtaining a panoramic dental radiograph while imposing the filter, wherein the imposing enhances the contrast of the radiograph in the region of carotid artery; and detecting a calcification region in the area of the radiograph wherein the x-ray image's contrast has been enhanced by using the filter, and which area corresponds with the location of the carotid artery. The suite of filters include a patient format, a cassette format, an x-ray unit format and a software-based format.

5 Claims, 8 Drawing Sheets

CAROTID ARTERY FILTER SYSTEM FOR SINGLE VIEW DENTAL PANORAMIC RADIOGRAPHS

BACKGROUND OF THE INVENTION

Stroke is the third largest cause of death in the United States. Over 700,000 strokes occur annually in the United States at an estimated cost of $40 billion annually. Of these, half are believed to be due to emboli originating at the carotid bifurcation. Large, multi-institutional trials confirm that surgery improves overall survival and stroke rates as compared to medical management for high-grade stenoses.

Duplex ultrasound (DUS) is one of the safest tests for the identification of significant degrees of carotid stenoses. While accurate, and safe, a high-quality DUS requires 20–40 minutes of technician time, formal physician interpretation, and costs several hundred dollars. Based on some studies, screening entire populations, even those limited to patients over 65, may be cost-ineffective unless the prevalence of carotid stenoses is at least 4.5%.

Many patients undergoing dental examination and/or treatment undergo panoramic radiography as part of their routine care. As is commonly known, a panoramic radiograph or an x-ray is an x-ray taken by a machine using a fixed and predetermined exposure setting that rotates around the head of a patient to give the dentists a picture of the patient's teeth, jaws and other important information. These radiographs (x-ray images) include, in most cases, the region of the carotid bifurcation on the sides of the resulting x-ray image. It has recently been noted that incidental calcifications can be visualized if adequate attention is paid to this area. Data suggest that the rate of clinically significant carotid disease may be high enough to make examination of this region on otherwise routine panoramic radiograph, followed by DUS, if positive, a clinically beneficial approach.

Initial research was carried out to understand the correlation between incidental findings on single view panoramic radiographs positive for carotid artery calcifications and clinically critical carotid stenoses. Data from the initial research suggest that the prevalence of clinically significant stenosis among patients for whom calcifications are observed on single view panoramic radiographs may be quite high; certainly well in excess of the 4.5% prevalence threshold at which the use of the DUS as a screening tool becomes cost effective.

The yielding of substantial public health benefits by being able to detect significant carotid stenoses using a single view panoramic radiograph depends in part on the improvement of the diagnostic quality of the panoramic radiograph or x-ray system. Intra and inter-examiner variability and misinterpretation of the carotid artery bifurcation have been proven to be dependent on the diagnostic quality of the x-ray image, suffering from the nature of the film/screen/imaging media configuration.

As panoramic radiographs were primarily designed to diagnose disease in the hard tissue regions within the maxillofacial region, soft tissue regions, such as those in the carotid artery region, tend to get overexposed or "burned," when imaged using a single view panoramic radiograph. Radiographic filters exist to help improve contrast in radiographs of many types. While these filters tend to provide specificity and morphology, such filters tend to be site specific and unique in their filtering or contrast enhancing capabilities.

Therefore, in an effort to improve radiograph contrast and image quality in the carotid artery region, there is a need to develop a filter system for the carotid artery region.

BRIEF SUMMARY OF THE INVENTION

The use the carotid artery filter system in accordance with the present invention along with a routine panoramic x-ray examination, can have a widespread impact and will improve the diagnostic quality of a rather routine dental exam. The use of the carotid artery filter system in conjunction with a panoramic x-ray will improve the procedure's predictive value for carotid disease, prompt further evaluation of carotid disease with duplex ultrasound, and ultimately it will improve overall community health through better identification of a potentially life-threatening condition.

In one aspect, embodiments of the present invention are directed to a method of detecting carotid artery calcification in a panoramic dental radiograph, including imposing a filter between an x-ray radiation beam source and an imaging medium, wherein the imposing attenuates the effect of the incident x-ray in the region of the carotid artery; obtaining a panoramic dental radiograph while imposing the filter, wherein the imposing enhances the contrast of the radiograph in the region of carotid artery; and detecting a calcification region in the area of the radiograph wherein the x-ray image's contrast has been enhanced by using the filter, and which area corresponds with the location of the carotid artery.

In another aspect, various embodiments of the present invention are directed to various filters, including x-ray filters that may be used in conjunction with a panoramic x-ray device to enable the imaging of the carotid artery and the carotid bifurcation. These various filtering devices include a patient format, a cassette format, an x-ray unit format and a software-based format.

One embodiment of the filter device in accordance with the present invention is directed towards a carotid artery x-ray filter patch for use with a single view dental panoramic radiograph, including a backing layer; a filter layer disposed on the backing layer; and a cover layer disposed on the filter layer, the filter patch being configured to be placed on a patient's neck in a region substantially covering the carotid bifurcation while a single view dental panoramic radiograph of the patient is being generated.

Another aspect of the filter device in accordance with the present invention is directed towards a filter for enhancing a single view dental panoramic radiograph on a film contained in an x-ray cassette, wherein the film is responsive to an intensifying screen placed adjacent to the film, including a sheet interposed between the film and the intensifying screen, the sheet having an optically opaque portion overlaying the film in an area that is substantially in alignment with the patient's carotid artery, whereby an image produced in the film depicts hard tissue structures in the area not aligned with the opaque portion and soft tissue features including the carotid bifurcation in the area aligned with the optically opaque portion.

Another aspect of the filter device in accordance with the present invention is directed towards a carotid artery x-ray filter system for use with a single view dental panoramic radiograph device, including a filter support structure coupled with an x-ray outlet aperture of the panoramic x-ray device; an x-ray filter supported by the filter support structure; a positioning mechanism coupled with the filter support structure to position the filter in front of the aperture to selectively engage the x-ray beam as the beam is directed towards the carotid artery, whereby a resulting radiograph depicts hard tissue structures in the area not filtered by the x-ray filter and soft tissue features in the area filtered by the x-ray filter.

Another aspect of the filter device in accordance with the present invention is directed towards a varying filter region wherein the filter layer has a maximum filtering effect and further comprises a varying filter region extending inward from an edge towards a center of the filter, the varying filter region being configured to have a minimal x-ray filtering effect at the edge and a maximum filtering effect away from the edge, and wherein the maximum filtering effect in the filtering region is substantially equal to the maximum filtering effect of the filter layer.

For a further understanding of the nature and advantages of the present invention, reference should be made to the following description in conjunction with the accompanying drawings.

DETAILED DESCRIPTION OF THE INVENTION

Embodiments of the present invention provide a filter system that permits x-ray films or imaging devices (e.g., CCD or CMOS sensor arrays) in a panoramic radiograph device to be exposed at discreet intensities for different portions of a subject. This filter system is essential when imaging the dental structure of humans where the density of the human bone and teeth structure and soft tissue of the carotid bifurcation region vary considerably. The filter system in accordance with embodiments of the present invention enable the selective attenuation of an x-ray beam for different portions of a subject to ensure that the resulting image has the appropriate level of contrast to enable the imaging of the carotid artery, while not adversely impacting the diagnostic effectiveness of a normal panoramic radiograph. Embodiments of the filter system of present invention work in conjunction with a panoramic x-ray machine having a preset exposure setting to selectively filter the carotid artery bifurcation region. The carotid artery bifurcation region includes the region near the common carotid artery (CCA). The carotid artery is a key artery located in the front of the neck that carries blood from the heart to the brain. Cholesterol plaque on the inner wall of the carotid artery and/or the carotid bifurcation can lead to stroke. The two CCAs are the principal arteries supplying the structures of the head and neck. They ascend in the neck, one on each side, and at the level of the upper border of the thyroid cartilage, each bifurcates into two branches, the external carotid artery (ECA) and internal carotid arteries (ICA).

Figure 1:
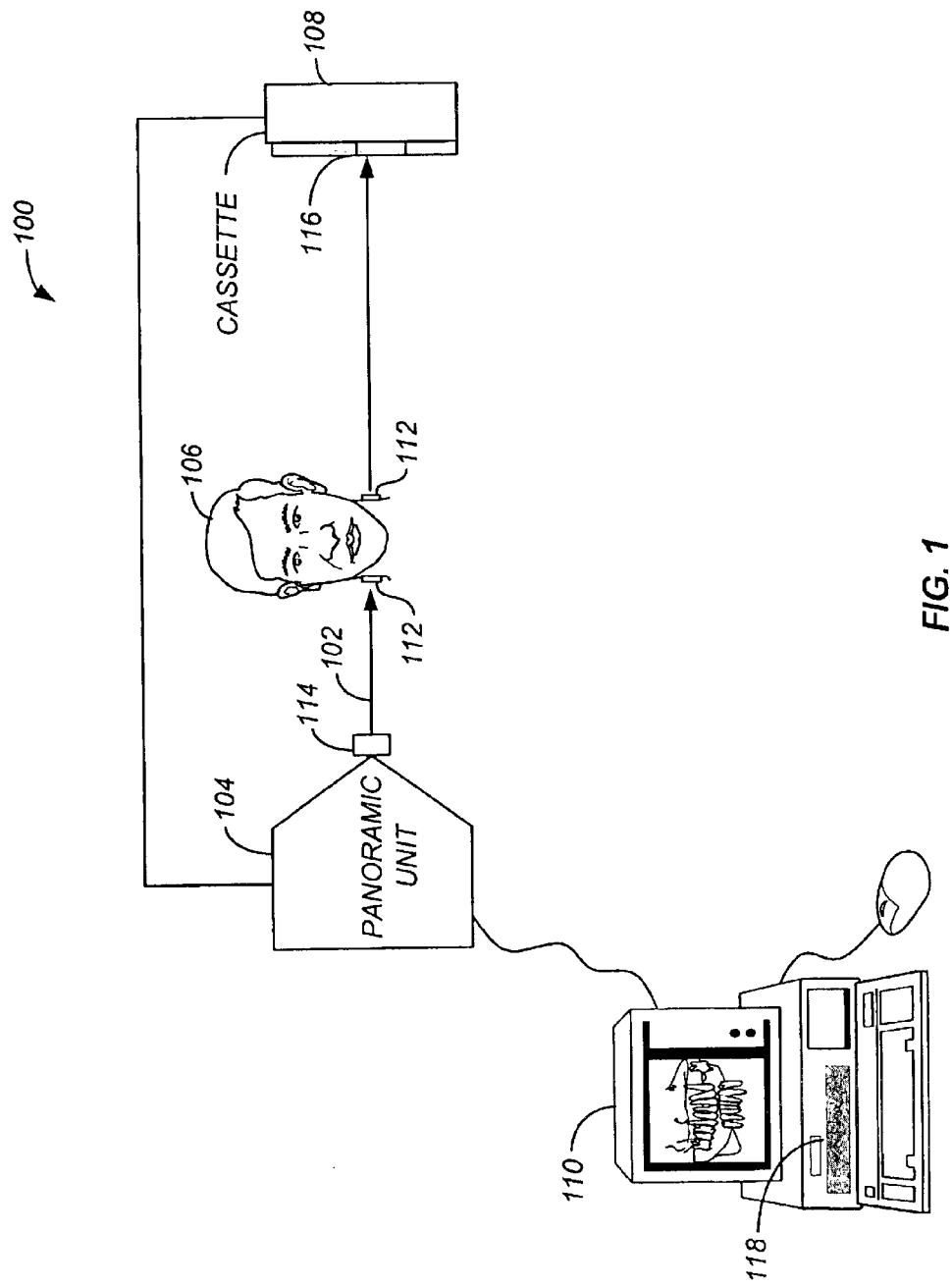
FIG. 1 is a diagrammatic view of a typical imaging set up.

FIG. 1 shows a diagrammatic view of a typical imaging set up 100. A typical single view panoramic x-ray device is used to create an x-ray image taken by a machine at a fixed and predetermined exposure setting, where the machine rotates around the head of a patient to give the dentist a picture of the patient's teeth, jaws and other important information. The exposure setting is preset to optimally image the hard tissue regions, such as the teeth and the jaw bone. A typical single view panoramic radiograph system includes a panoramic unit 104 and a cassette 116 which is subjected to exposure from an x-ray radiation beam 102. The patient 106 is positioned between the radiation source 104 and the cassette 116. Typically, the cassette holds the film and the accompanying intensifying screens as is generally known to those having skill in the x-ray imaging arts. Alternately, in addition to or in place of the film in the cassette, there may be disposed an electronic imaging device such as, for example, a CCD or CMOS image sensor array that is exposed to the beam passing through the patient to create an electronic image. When using an electronic imaging device, the x-ray unit (e.g. 104 and 108) may be coupled with a host computer 110 that manages the image processing, including the display of the captured radiograph. The carotid bifurcation filter system according to embodiments of the present invention encompasses several embodiments, including a patient filter patch 112, a cassette format filter 116, a unit format filter 114 and a software-based filter 118. In either of these embodiment, the x-ray filter has regions of different filter densities which act to reduce the overexposure or burning of the carotid bifurcation regions in the resulting image. The use of the carotid artery filter system enhances the contrast of the resulting panoramic x-ray images by attenuating the effect of the incident x-ray and thus avoids the over exposure of the imaging media in the region of the carotid artery, to enhance the contrast in the filtered regions. By avoiding the over exposure of the media and enhancing the contrast in the filtered regions, the carotid filter system enables and improves the detection of calcification in the carotid artery region in a resulting x-ray image. Once a calcification in or near the carotid artery is identified in a panoramic dental x-ray, the patient is further screened, for example, by using a DUS procedure.

The carotid bifurcation filter system according to embodiments of the present invention is useful for single view dental panoramic images, particularly taken on individuals 40 years or older and more preferably 55 years of age or older, who are incidentally at higher risk for carotid stenosis that may lead to stroke. Carotid calcifications seen on a panoramic dental radiograph should prompt further evaluation of carotid disease with duplex ultrasound.

Various embodiments of the carotid filter system including a patient format, a cassette format, an x-ray unit format and a software-based format, are each described below in further detail.

Patient Format—Carotid Patch

Figure 2A:
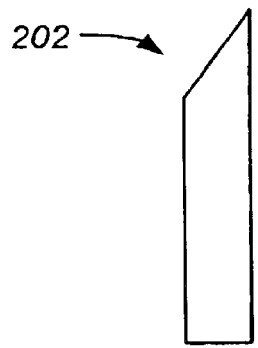
FIG. 2A is a diagram of a cross-section of the carotid x-ray filter of FIG. 2.
Figure 2:
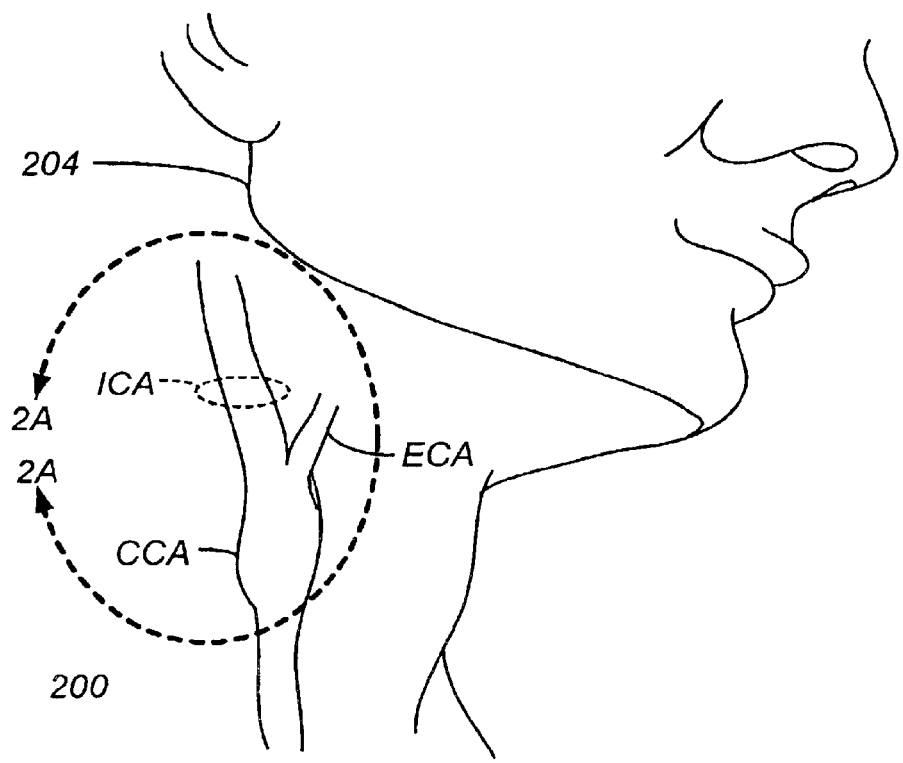
FIG. 2 is a diagram of the patient format carotid patch filter in accordance with an embodiment of the present invention.

FIG. 2 shows an external x-ray absorptive shield material placed between the x-ray source and the patient. This embodiment of the x-ray filter 200 is configured to be worn by a patient so as to cover generally the area of the neck over the carotid bifurcation. In one embodiment, a thin pear-shaped, plate-like filter layer is adhered to the right and left sides of the neck, below and distal to the angle of the mandible 204 bilaterally corresponding with the carotid bifurcation regions. Although a pear or egg-shaped filter patch is shown, any other suitable shape is within the scope of the presently described filter patch. Other configurations, such as circular, oval, rectangle, triangle, etc. are all equally suitable for the overall shape of the filter. For example, an L-shaped patch is also suitable, where the vertical portion of the L is directed towards the back of the ear of the patient and the horizontal portion is aligned with the horizontal portion of the mandible and where the angle of the L is aligned with the angle of the mandible. An essential aspect of the shape of the patch format filter is that it should cover the carotid artery area when place on the patient. And as an aid to the x-ray technician, a pear-shaped or egg-shaped patch is easily placed on the neck of a patient and so long as the pointed or narrow end is pointed towards the mandible angle, the technician can be assured that the patch is sufficiently covering the carotid region.

FIG. 2A is a diagram of a cross-section of the carotid x-ray filter of FIG. 2. In an embodiment, the filter layer thickness 202 is tapered and feather edged upwards towards the bony structure of the lower jaw 204. In this manner, the attenuation or filtering achieved by the carotid filter is at a maximum value away from the edge of the filter that is near the bony structure, and as the filter thickness gets tapered down so too does the filtering effect of the carotid filter. The motivation for having the filter be tapered down is to ensure that a resulting radiograph image has an enhanced contrast in the area that is covered by the filter, while avoiding producing a visible line of demarcation between the filtered and unfiltered areas of the resulting panoramic radiograph. It is desirable to avoid a visible line of demarcation to avoid adversely affecting the diagnostic effectiveness of the resulting panoramic radiograph.

The tapering of the filter's edge may be achieved by fabricating the taper structure, for example, by a molding or a stamping process. Alternately, the tapered shape may be achieved by forming the x-ray filter by forming the filter as a series of stacked filter layers that are arranged in an offset manner to form a stepped edge thus forming the tapered edge. An additional advantage of the stacked filter embodiment is realized when each filter layer in the stack is peelable with respect to its adjacent layers. In this manner the stacked arrangement enables an enhanced control over attenuation ratio, where attenuation or the resulting radiograph contrast is adjusted by pealing back layers to reduce the effective thickness of the x-ray filtering layers depending on a patient's size.

Figure 3:
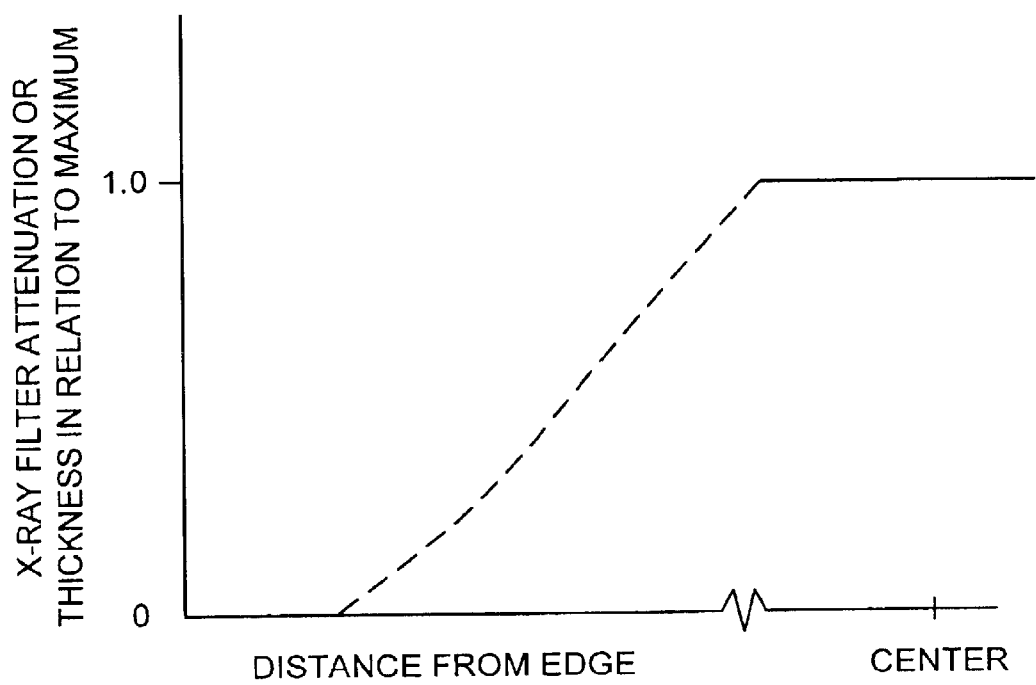
FIG. 3 is a graph of attenuation vs. distance from the edge of an x-ray filter in accordance with an embodiment of the present invention.

An alternate manner of achieving the tapered edge effect is to fabricate the filter as a composite layer, where an x-ray filter material that is in a granular or powder form is used to impregnate a substrate. In this manner, the taper effect may be fabricated by reducing the filter material's concentration from a maximum value away from the edge to minimum value at the edge. An essential aspect of the feathered edge is that the filter be fabricated into a thin plate or sheet having a very thin or very lightly absorbing edge (the feather edge) and an increasing (e.g., uniformly) thickness away from such edge and a higher attenuating region away from the edge, as is shown in FIG. 3. Note that the tapered filtering may be achieved by either tapering the filter's thickness or varying the material concentration of the filtering material near the edge, or by varying the material property of the filtering material in the tapered filtering region of the x-ray filter.

The desired filtering effect is a function of the desired resulting contrast, which is a function of the intensity of the x-ray that is incident on the imaging media. So, for example, if it is desired to enhance the contrast on the media in the regions of interest by a factor of two, then the filter is chosen to attenuate the x-ray beam by a factor of two in the desired region (i.e., the region of the carotid artery). Other levels of contrast are achieved by adjusting the x-ray filter's effectiveness. For a given x-ray filter material, say for example, aluminum, the filter's effectiveness is increased by increasing the thickness of the filter layer, as is commonly known and which is in accordance with the generally exponential nature of the attenuation of an x-ray beam.

Alternately, when the x-ray filter material is fabricated as a composite layer as described above, the effectiveness of the x-ray filter may be adjusted by increasing or decreasing the concentration of the x-ray filtering material within the underlying or surrounding substrate.

The x-ray attenuating or filtering patch may be composed of a material that is capable of attenuating x-ray radiation to a desired degree when formed into a thin layer. Possible materials include suitably dimensioned solid metal sheets and composite sheets impregnated with fine metallic powders or oxides or salts of heavy elements, such as, for example, lead oxide, lead sulfate or lead sulfide. The absorption of the x-ray radiation by a material is proportional to the degree of x-ray attenuation and is dependent on the energy of the x-ray radiation and the following material parameters, namely: thickness; density; and the atomic number. Generally the lower the atomic number the more transparent the material is to the x-rays. Materials composed of elements with a high atomic numbers absorb radiation more effectively causing darker shadows in an X-ray image. Substances with low atomic numbers absorb less x-ray radiation, hence their shadowgraph appears a lighter color. While aluminum and copper are common filter materials, other filter materials such as tin, lead, molybdenum, rhodium, rare earth materials, yttrium, gadolinium and ytterbium, as well as filters made of gases contained within objects or substrates may also be used.

In one embodiment, the carotid patch is fabricated by sandwiching the x-ray filter material between a backing layer and a covered adhesive layer. Thus, a clinician or an x-ray technician can simply peel back the cover from the adhesive layer and adhere the patch to the patient below and distal to the angle of the mandible as is shown in FIG. 2, much like how an adhesive bandage or a nicotine patch is affixed to a person's body. In this manner, the resulting radiograph will be able to better show the region which is being scanned for carotid stenosis. This region includes the region near the common carotid artery (CCA).

The patient-patch carotid filter is a very simple way for achieving the desired additional attenuation of the x-ray beam to result in a single view panoramic x-ray having sufficient contrast to be able to better show a carotid artery calcification. Its use is simple because by simply placing (and optionally adhesively attaching) the filter patch on the neck of the patient below the patient's angle of the mandible, it obviates the need for any more complex positioning and placement structures. The x-ray technician operating the panoramic x-ray machine does not need to make any additional adjustments (e.g., for exposure settings) to the panoramic x-ray device's set up, other than simply placing the patch in the patient's neck region as is shown in FIGS. 1 and 2.

An alternate embodiment of the carotid filter system of the present invention works in conjunction with a typical x-ray film and its accompanying x-ray film cassette, which is described below in further detail.

Cassette Format—Carotid Filter

An alternate embodiment of the carotid filter system includes a filter material positioned in the x-ray cassette that is used to hold the x-ray film. Normal film cassettes provide an image on the x-ray film by placing the film having one emulsion side against one conversion screen or having two emulsion sides between two conversion screens. The conversion screens convert incident x-radiation into energy having a wavelength that effectively reacts with a film sensitive to that wavelength. For example, if the film is sensitive to blue light, the conversion screen will be formed to produce blue light in response to x-ray radiation with the intensity of the light being a function of the x-ray intensity. A conversion screen has a uniform response characteristic. That is, if the screen is subjected to a uniform radiation intensity, it will produce an even exposure in the film adjacent to it. Commercially available cassettes that may be configured to practice the embodiments of the present invention include 5×12 and 6×12 inch screens with rare earth screens that are green sensitive, as well as blue sensitive screens and other as are known to those being skilled in the x-ray imaging arts.

Figure 4:
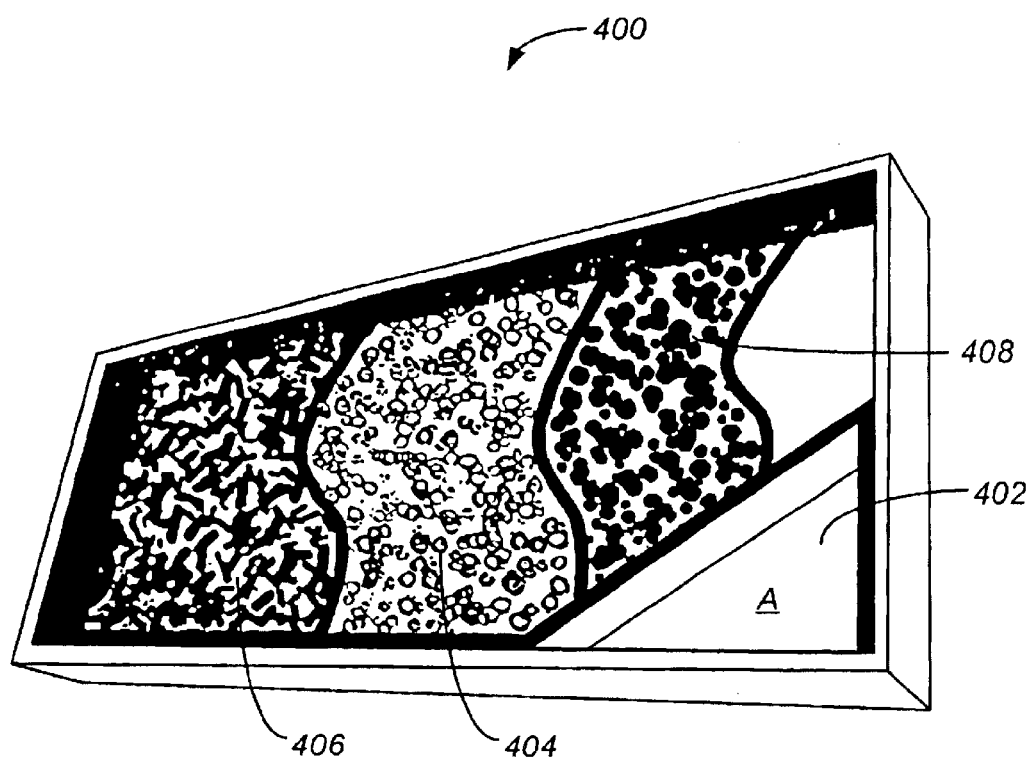
FIG. 4 is a diagram of the cassette format carotid filter in accordance with an embodiment of the present invention.

FIG. 4 is a diagram 400 of the cassette format carotid filter in accordance with an embodiment of the present invention. In this embodiment, the carotid bifurcation filter layer 402 is triangle shaped, thin and plate-like. Alternately, the filter is a one-piece filter having generally the same size as the x-ray film so as to enable a technician to easily place it within the cassette. The alternate or one-piece filter will be completely transparent except for the two lower corner triangular regions which are more opaque so as to selectively filter x-rays and improve contrast in the area near and around the carotid artery. Alternately, the opaque regions or the triangular filter is also tapered and feather edged towards the bony structure of the lower jaw in order to avoid producing a visible line of demarcation between the filtered and unfiltered areas of the resulting panoramic x-ray image. Yet alternately, instead of tapering and feather edging the filter, the opacity of the filter in the "taper" region is adjusted so that at the edge near the bony structure the opacity is nearly zero and the opacity gradually increases from this near zero value to a maximum value in the non-"tapered" region. An essential factor of the "taper" region is that the filtering or attenuation is minimal at the location near the bony structure of the jaw and maximum in the region covering the area of the potential carotid calcification. Using this tapering ensures that the resulting x-ray image shows any calcification within the carotid artery region, while still maintaining and not adversely impacting the original diagnostic purpose of the single view panoramic x-ray image.

The triangular shaped filter is a preferred shape because of its ease of fabrication and placement in the x-ray cassette. While the triangular shape is a preferred shape, other shapes are also within the scope of the embodiment of the cassette-based filter. These other shapes include alternative shapes described above in relation to the patient patch filter. The actual geometry of the filter may take on many shapes, so long as the filter when used with the film results in an improved contrast in the region of the carotid artery to enable the imaging of the calcification in or near the carotid artery.

Referring to FIG. 4, in one embodiment, the x-ray filter 402 is placed in between the x-ray film 404 and the intensifying screens 406 and 408. As is shown in FIG. 4, the carotid filter is positioned inside the cassette, sandwiched behind the front intensifying screen 404, or in front of the back intensifying screen 4048, behind the x-ray film. After being exposed to radiation, the reactant materials of the intensifying screen are activated to cause the film to record an image approximating the structure through which the radiation has passed. A screen layer, and hence the filter adjacent thereto may be positioned adjacent to either side or both sides of the x-ray film. Adhesive tabs mounted on the optical filter can facilitate the attachment of the filter against the screen and thus help maintain in place while the film is placed in the cassette.

In the cassette embodiment, where the filter layer is placed between the intensifying screen and the x-ray film, the preferred filter material absorbs energy in the optical spectrum, preferably at least one of blue and green, and as such the material is a relatively green-blue colored material, and thus is consistent with that of the intensifying screens. While an exemplary filter is described with reference to inhibiting blue, green, and combinations thereof, a filter having a different characteristics is also possible. For example, the filter material may be chosen to be different from the blue or green colors and chosen to attenuate the light reaching the film by the desired ratio to effectively improve the contrast in the carotid artery regions. The filter may be designed to have multiple different optical characteristics. The cassette-based carotid filter can be implemented in several ways, including a built-in filter that is placed in the cassette as described above. Alternately, the cassette-based filter may be positioned by an operator any time a carotid bifurcation calcification risk individual is being imaged.

Alternately, the carotid filter may be incorporated into the conversion or intensifying screen, to selectively alter the screen's conversion of incident x-ray radiation into the optical spectrum to effectively expose the film to a non-uniform optical intensity.

Yet alternately, instead of interposing the filter between a conversion screen and the film, the filter may be placed in the x-ray beam path before it impinges on the outermost screen, or the cassette. In this alternate embodiment, since the filter is being used to attenuate the x-ray beam and not the optical beam (i.e., converted by the screen), the filter is fabricated in a manner and of materials that are similar to the x-ray filter of the patient-patch filter described above. An alternate approach also includes the use of an x-ray film having different emulsions in areas that correspond and align with the region of the carotid bifurcation. In this manner, effectively, the film and the filter are combined.

An alternate embodiment of the carotid filter system of the present invention is coupled with a typical panoramic x-ray unit, and is described below in further detail.

X-ray Unit Format—Carotid Filter

Figure 5:
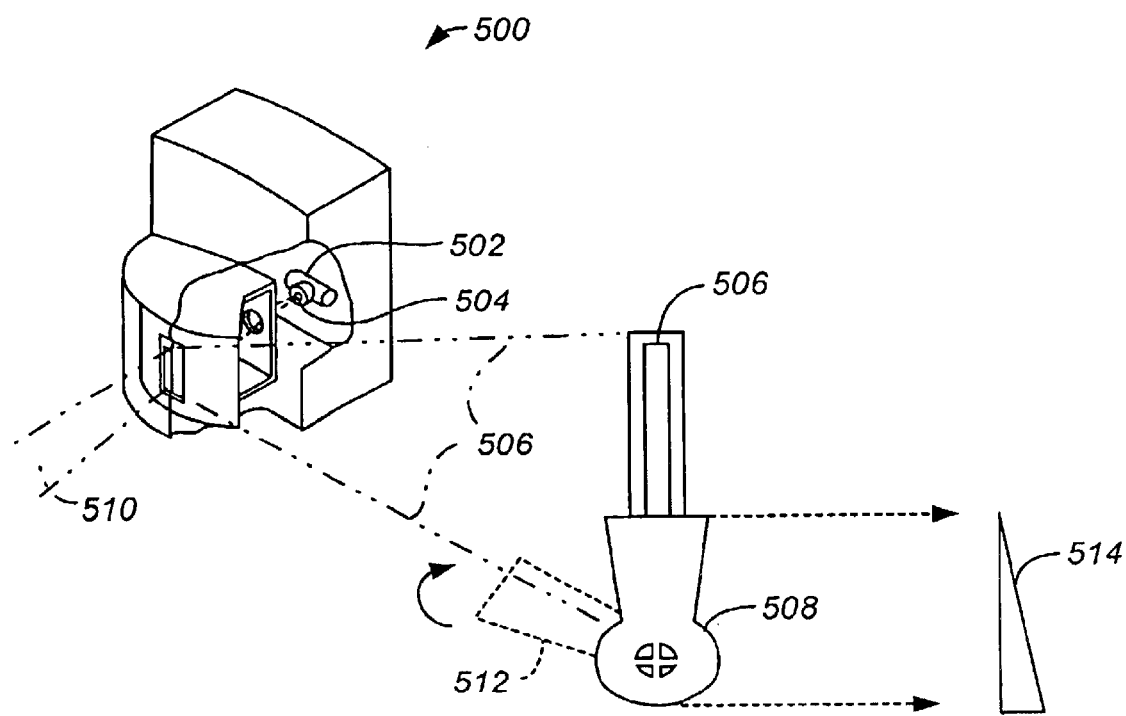
FIG. 5 is a diagram of the panoramic unit format carotid filter in accordance with an embodiment of the present invention.

In the x-ray unit format, an electronically or manually controlled filter mechanism is configured to be bilaterally engaged to partially block the bottom portion of the unit's aperture, thus blocking the x-ray beam portion, corresponding with the carotid bifurcations regions. In one embodiment, the filter is tapered in shape and feather edged upwards towards the bony structure of the lower jaw in order to avoid producing a visible line of demarcation between the filtered and unfiltered areas of the resulting image. FIG. 5 is a diagram 500 of the panoramic unit format carotid filter in accordance with an embodiment of the present invention. As is shown in FIG. 5, the panoramic x-ray unit includes an x-ray tube 502 that generates x radiation. The x radiation passes through aperture 506 to direct an x-ray beam 510 towards a patient and then towards an imaging media such as, for example an x-ray cassette or a photoarray (e.g., a CCD or a CMOS array).

The carotid bifurcation filter 508 is coupled with the aperture 506 and is configured to be selectively interposed between the beam and the patient. When the filter 508 is engaged, it is configured to attenuate the emerging x-ray beam so as to reduce the intensity of the beam that is incident on the imaging media to selectively filter the x-ray beam and hence increase the contrast of the resulting image to enable the imaging of the carotid arteries to allow any calcification within the carotid arteries to be captured in the resulting image. However, it is not desirable to leave the filter interposed between the beam and the patient during the entire range of the travel of the panoramic x-ray device around the patient, as this would interfere with and reduce the beam's energy in the hard tissue areas and thus adversely impact the diagnostic effectiveness of the panoramic x-ray device for the imaging of the hard tissue regions.

Therefore, the unit-coupled carotid filter is engaged only part of the time where the x-ray beam is directed towards the region of the carotid arteries and disengaged the remainder of the time when the beam is not directed toward the region near the carotid arteries. For example, as is shown in FIG. 5, the filter is mounted on a mount and can toggle between an engaged position 508 and a disengaged position 512.

Figure 6:
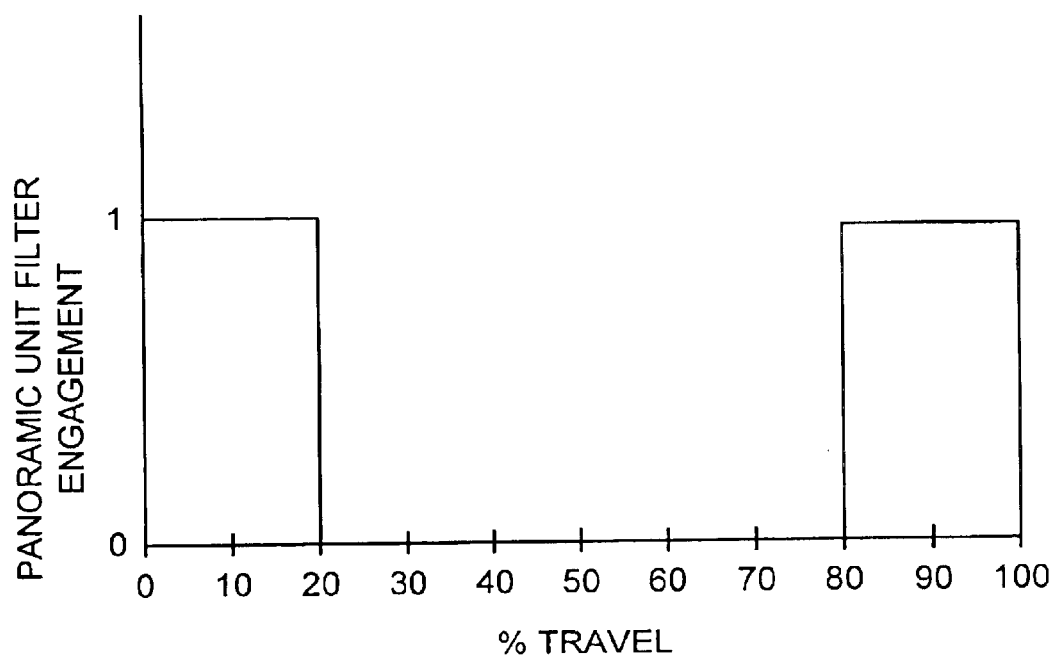
FIG. 6 is a graph of the panoramic unit format carotid filter engagement vs. travel.

An example of the engagement of the filter as a function of the travel of the x-ray device around an individual is shown in FIG. 6. As can be seen from this figures, the filter is engaged during the initial portion of the travel for approximately 20% of the travel, and then the filter is disengaged and then again engaged for the last 20% of it's travel. In this manner, the filter is initially engaged as the taking of the x-ray image initiates just past the corner of the jaw of the patient. Then, as the beam travels beyond the region of the carotid arteries, the filter is disengaged so to not interfere with the imaging of the jaw bone and teeth. Then, as the beam begins to approach the region of the carotid artery on the opposing side of the neck, the filter is again engaged.

Various automatic or manual mechanisms may be used to cause the selective engagement of the filter as it is coupled with the x-ray device's aperture. One mechanism, for example can include a controlled motor drive coupled with the filter assembly to rotate the filter into and out of the beam. The motor drive can be configured to receive an input similar to that of FIG. 6 to selectively engage and disengage the filter as the x-ray unit travels around the patient from one side to the other.

The material for the x-ray filter can include aluminum or copper having a thickness to result in an appropriate contrast in the final image to enable the imaging of the soft tissue regions near the carotid arteries. Furthermore, the filter may be fabricated as is set forth above for the patient-format carotid patch x-ray filter. Additionally, the filter's thickness or its effective attenuation is preferably tapered and/or feather edged 514 to ensure that there is no line of demarcation between the filtered and unfiltered areas of the image so as not to adversely impact the panoramic x-ray images dental diagnostic effectiveness. The tapering or graduated filtering region of the filter may be fabricated using fabrication methods that are similar to those described above for the patient-format carotid patch x-ray filter.

Software Filtering or Exposure Control

An additional alternate method of filtering the preset x-ray beam of a single view panoramic x-ray is an electronic or software-based approach. In some x-ray imaging devices, the x-rays from the patient energize a photoarray (e.g., a CCD or a CMOS array) that is coupled with a computer system for processing the x-ray image. With such a computer-coupled x-ray device, it is possible to enhance portions of the image so that the soft tissue near the region of carotid arteries appears with an appropriate level of contrast in the final image. Such a computer or software-based filtering includes computer readable instructions for enhancing the resulting image's contrast in the regions of interest to enable the detection of calcification regions near the carotid bifurcation. Such instructions include instruction for selecting a region of a given shape, and instruction for adjusting the contrast of the produced image in the selected region. The selected regions can have any shape including a triangular region, as well as other shapes as set forth above. Additionally, the adjusting (of contrast) in the selected region may alternately be performed in a manner to ensure that there is no visible line of demarcation between the selected and the non-selected regions. One way of achieving this avoidance of lines of demarcation is to vary the contrast adjustment so that it is effectively tapered; having a maximum adjustment away from the boundary between the selected and the non-selected region and having a gradually varying contrast adjustment from this maximum value to a minimum value at the boundary between the selected and the non-selected regions.

Figure 7:
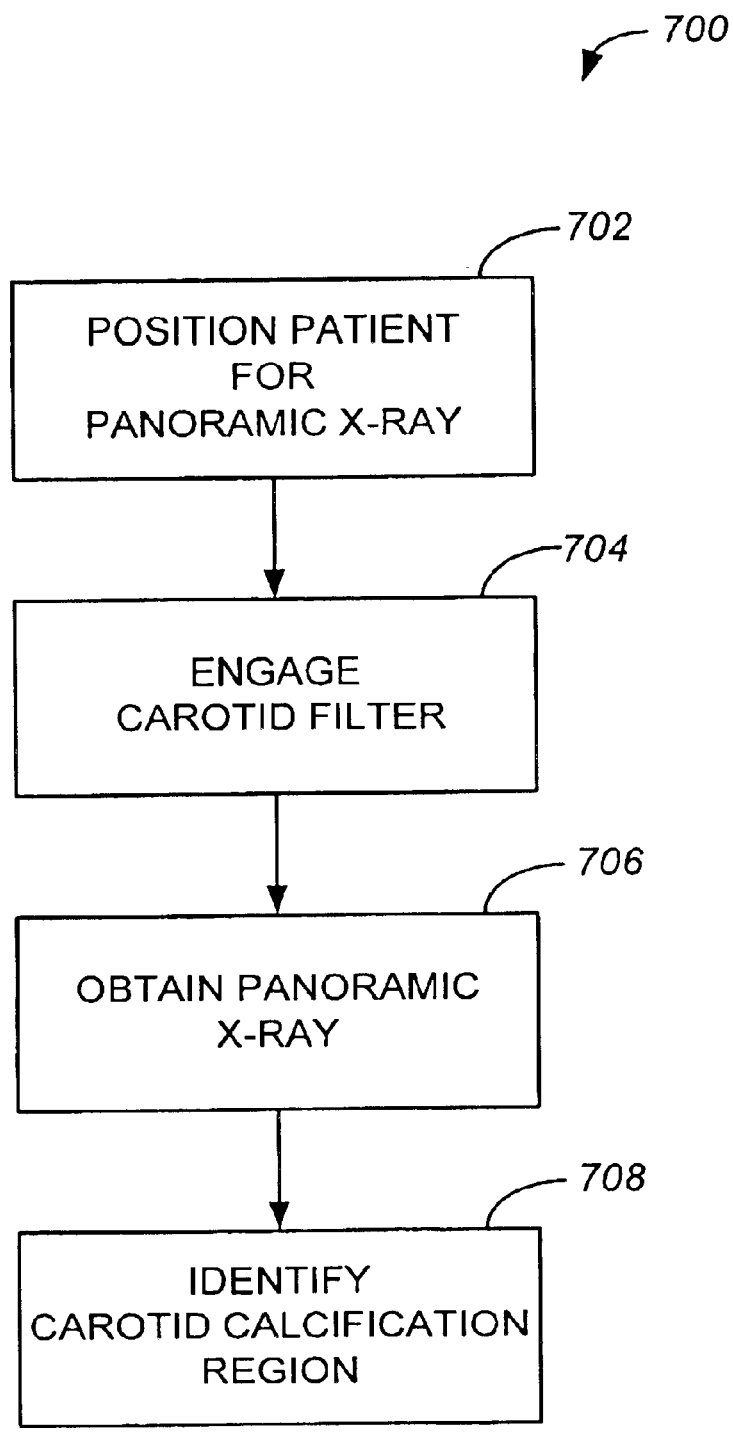
FIG. 7 is a flow chart of a method of obtaining a filtered single view panoramic x-ray image showing the carotid bifurcation region as well as the bony structure of the jaw and the dental structure.

Method of Obtaining a Single View Panoramic X-ray to Also Image the Carotid Arteries FIG. 7 is a flow chart 700 of a method of obtaining a filtered single view panoramic x-ray image showing the carotid bifurcation region as well as the bony structure of the jaw and the dental structure. In order to obtain such an image, the patient is appropriately positioned 702. Next, the technician engages the carotid filter system 704. The carotid filter system may include any one of the filter embodiments described above, namely the patient patch, the cassette filter, the unit-coupled filter and the software-based filter. Having engaged the carotid filter system, the panoramic x-ray device is used to generate a single view panoramic x-ray 706. An example of a panoramic x-ray machine that may be configured to practice the teachings of the present invention is a Panoral model A4 unit from Sybron Ritter Corporation of Rochester, N.Y. The unit is typically operated at 6 to 8 mA and 75 to 90 KVp, where the setting may be varied depending on the patient's estimated jaw size. In this unit, Kodak dental film (e.g., DFG-5) with Kodak X-Omatic regular intensifying screens may be used. Other examples of panoramic x-ray machines that may be configured to practice the teachings of the present invention include panoramic x-ray machines from Planmeca Group; Panoramic Corporation; Instrumentarium Imaging Inc. and Sirona's Orthopos machines. Exposed panoramic radiographs may be processes according to the manufacturer's recommendation, for example, in an A/T 2000 automatic film processor such as one from Air Techniques Inc., of Kicksville, N.Y. An alternate exposure setup that may also be used to practice the teachings of the present invention has an exposure setting of 16 Ma at 64 KVp for a scan period of 14 sec. Yet another possible setting is an exposure setting of 73 KVp at 15 ma for 14 seconds. The common factor between all these x-ray machines is that their exposure setting is chosen to image the hard tissue region of the jaw bone and teeth and not the soft tissue regions near the carotid arteries. Using such setting will tend to over expose the soft regions of interest if used without the carotid filter system in accordance with embodiments of the present invention. Using the generated image, a clinician may then detect any calcification that may be present within the carotid region 708.

Figure 8:
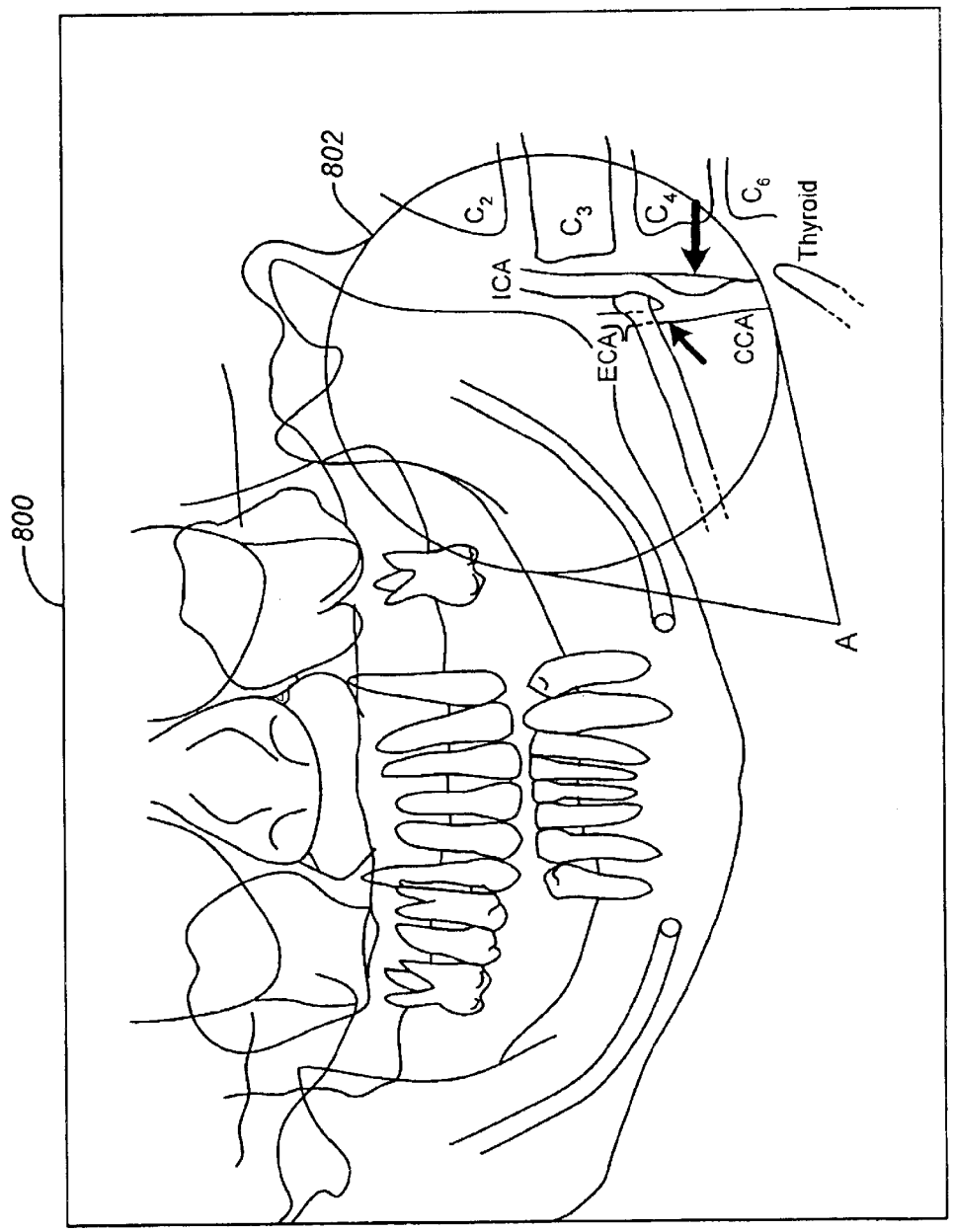
FIG. 8 is an idealized x-ray image obtained using a panoramic x-ray device while using the carotid filter system in accordance with embodiments of the present invention.

FIG. 8 is an idealized x-ray image 800 obtained using a panoramic x-ray device while using the carotid filter system in accordance with embodiments of the present invention. The image displayed by FIG. 8 includes the radiographic image intended to be captured by a panoramic x-ray device (i.e., hard tissue structures of the jaw bone and dental structures) and images of soft tissue regions to highlight features of interest (i.e. carotid artery region). Such an image enables the detection of carotid artery calcifications. Such an x-ray image includes region 802, which includes the softy tissue regions of the carotid arteries. This figure (FIG. 8) shows the relationship of the CCA, ICA, ECA and the structures usually seen on a panoramic radiograph. This figure is capable of showing the embolization of atherosclerotic debris (thick arrow) at the Cortaid bifurcation (thin arrow). A panoramic radiograph taken using embodiments of the carotid filter system of the present invention is able to reveal the presence of radiopacities lying over either or both carotid bifurcations. Calcifications may be located inferior to the angle of the mandible and the tip of the hyoid bone and superior to the tip of the thyroid cartilage and the C3, C4 and C5 vertebrae.

The use of carotid filters in accordance with embodiments of the present invention has several advantages. First, using the carotid filter in accordance with embodiments of the present invention will improve the diagnostic realm and quality of an otherwise routine dental exam. Second, embodiments of the present invention will improve the positive predictive value for carotid disease and prompt further evaluation of carotid disease with, for example, duplex ultrasound. Additionally, embodiments of the present invention will improve overall community health through better identification of a potentially life threatening condition.

As will be understood by those skilled in the art, the present invention may be embodied in other specific forms without departing from the essential characteristics thereof. For example, the x-ray filter may be fabricated of any material having an appropriate thickness and/or material property to enhance the contrast in the resulting image to capture a potential carotid calcification. These other embodiments are intended to be included within the scope of the present invention, which is set forth in the following claims.

What is claimed is:

1. A carotid artery x-ray filter patch for use with a single view dental panoramic radiograph comprising:
    a backing layer;
    a filter layer disposed on said backing layer; and
    a cover layer disposed on said filter layer,
    said filter patch being configured to be placed on a patient's neck in a region substantially covering the carotid bifurcation while a single view dental panoramic radiograph of the patient is being generated, the carotid filter patch
    further comprising adhesive layer placed between said filter layer and said cover layer, such that the removal of said cover layer exposes said adhesive layer,
    said adhesive layer being configured to adhere to the patient's neck in a region substantially covering the carotid bifurcation while a single view dental panoramic radiograph of the patient is being generated.

2. The carotid artery x-ray filter patch of claim 1 wherein said filter layer is comprised of a material selected from the group consisting of aluminum, copper, tin, lead, molybdenum, rhodium, rare earth materials, yttrium, gadolinium and ytterbium, gases contained within objects or substrates, and combination thereof.

3. The carotid artery x-ray filter patch of claim 1 wherein said filter layer is an x-ray attenuator that when used in conjunction with a single view panoramic x-ray device causes an imaging medium in said panoramic x-ray device to be exposed to a different x-ray intensity for portions covered by said patch, so as to capture an image of the carotid artery which is substantially covered by said patch.

4. The carotid artery x-ray filter patch of claim 1 wherein said filter layer has a maximum x-ray filtering effect and further comprises a varying filter region extending inward from an edge towards a center of said filter,
    said varying filter region being configured to have a minimal x-ray filtering effect at said edge and a maximum filtering effect away from said edge, and wherein said maximum filtering effect in said filtering region is substantially equal to the maximum filtering effect of said filter layer.

5. The carotid artery x-ray filter patch of claim 4 wherein said varying filter region is a gradually varying filter region.

* * * * *